(12) United States Patent
Hacker et al.

(10) Patent No.: US 9,155,462 B2
(45) Date of Patent: Oct. 13, 2015

(54) SHORT COHERENCE INTERFEROMETRY FOR MEASURING DISTANCES

(75) Inventors: Martin Hacker, Jena (DE); Ralf Ebersbach, Schmoelln (DE); Thomas Pabst, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 47 days.

(21) Appl. No.: 13/000,276

(22) PCT Filed: Jun. 12, 2009

(86) PCT No.: PCT/EP2009/004264
§ 371 (c)(1),
(2), (4) Date: Dec. 20, 2010

(87) PCT Pub. No.: WO2009/153005
PCT Pub. Date: Dec. 23, 2009

(65) Prior Publication Data
US 2011/0109913 A1 May 12, 2011

(30) Foreign Application Priority Data
Jun. 20, 2008 (DE) .......................... 10 2008 029 479

(51) Int. Cl.
*G01B 9/02* (2006.01)
*G01J 5/60* (2006.01)
(Continued)

(52) U.S. Cl.
CPC ................ *A61B 3/1005* (2013.01); *A61B 3/102* (2013.01); *G01B 9/02079* (2013.01); *G01B 9/02091* (2013.01); *G01B 9/02097* (2013.01); *A61B 3/15* (2013.01); *G01B 2290/70* (2013.01)

(58) Field of Classification Search
CPC . G01B 2290/70; G01B 9/02091; A61B 3/102
USPC ............... 356/451, 453, 456, 491, 479, 497; 250/227.19, 227.27
See application file for complete search history.

(56) References Cited

U.S. PATENT DOCUMENTS 5,321,501 A * 6/1994 Swanson et al. .............. 356/479
5,347,328 A 9/1994 Sekine et al.
(Continued)

FOREIGN PATENT DOCUMENTS

DE 446 183 6/1927
DE 32 01 801 A1 9/1983
(Continued)

OTHER PUBLICATIONS

Bachmann et al. "Dual beam heterodyne ourier domain optical coherence tomography" Optics Express, vol. 15, No. 15; Jul. 23, 2007, pp. 9254-9266.*
(Continued)

*Primary Examiner* — Michael A Lyons
*Assistant Examiner* — Hina F Ayub
(74) *Attorney, Agent, or Firm* — Patterson Thuente Pedersen, P.A.

(57) ABSTRACT

A short coherence interferometer for measuring several axially spaced-apart regions of a sample, especially of an eye, which has a measuring optical path, through which the measuring radiation falls on the sample, a tunable interferometer for the axial, relative retardation of parts of the radiation, wherein the axial relative retardation is assigned to the axial spacing of the regions and a detector for producing an interference signal from interfering measurement radiation, scattered or reflected back from the sample as sample radiation. The tunable interferometer divides the sample radiation into two parts, which are axially relatively retarded and superimposed so as to interfere. During the superimposition, the tunable interferometer forms individual radiations, which represent quadrature components of the sample radiation, and the detector detects the individual radiations.

20 Claims, 3 Drawing Sheets

(51) Int. Cl.
*G01J 3/45* (2006.01)
*G01B 11/02* (2006.01)
*A61B 3/10* (2006.01)
*A61B 3/15* (2006.01)

(56) References Cited

U.S. PATENT DOCUMENTS

| | | | |
|---|---|---|---|
| 5,719,673 A | 2/1998 | Dorsel et al. | |
| 6,198,540 B1 | 3/2001 | Ueda et al. | |
| 6,657,727 B1 | 12/2003 | Izatt et al. | |
| 6,806,963 B1 | 10/2004 | Wälti et al. | |
| 7,126,693 B2 | 10/2006 | Everett et al. | |
| 7,145,661 B2 | 12/2006 | Hitzenberger | |
| 7,916,387 B2 * | 3/2011 | Schmitt | 359/344 |
| 8,396,536 B2 * | 3/2013 | Modell | 600/476 |
| 2002/0122181 A1 | 9/2002 | Koch et al. | |
| 2003/0020920 A1 * | 1/2003 | Dave et al. | 356/479 |
| 2004/0061865 A1 | 4/2004 | Drabarek | |
| 2004/0218189 A1 * | 11/2004 | Izatt et al. | 356/479 |
| 2004/0239943 A1 | 12/2004 | Izatt et al. | |
| 2005/0030548 A1 * | 2/2005 | Li | 356/497 |
| 2005/0099633 A1 * | 5/2005 | Failes | 356/479 |
| 2005/0140981 A1 | 6/2005 | Waelti | |
| 2005/0179907 A1 * | 8/2005 | Feldman | 356/489 |
| 2006/0109477 A1 | 5/2006 | Zhou et al. | |
| 2006/0171503 A1 | 8/2006 | O'Hara et al. | |
| 2007/0002327 A1 * | 1/2007 | Zhou et al. | 356/456 |
| 2007/0008545 A1 | 1/2007 | Feldchtein et al. | |
| 2007/0024856 A1 | 2/2007 | Izatt et al. | |
| 2007/0024860 A1 | 2/2007 | Tobiason et al. | |
| 2007/0239035 A1 * | 10/2007 | Nakabayashi | 600/476 |
| 2008/0165366 A1 * | 7/2008 | Schmitt | 356/519 |
| 2008/0285043 A1 | 11/2008 | Fercher et al. | |
| 2009/0027688 A1 | 1/2009 | Pouet | |
| 2011/0292395 A1 * | 12/2011 | Fercher et al. | 356/451 |

FOREIGN PATENT DOCUMENTS

| | | |
|---|---|---|
| EP | 1 750 086 A1 | 2/2007 |
| WO | WO 01/38820 A1 | 5/2001 |
| WO | WO 02/40936 A1 | 5/2002 |
| WO | WO 2005/062941 A2 | 7/2005 |
| WO | WO 2007/065670 A2 | 6/2007 |

OTHER PUBLICATIONS

Podoleanu, Adrian Gh., "Unbalanced versus balanced operation in an optical coherence tomography system," *Applied Optics*, vol. 39, No. 1, pp. 173-182 (Jan. 1, 2000).

Drexler, Wolfgang, et al., "Submicrometer Precision Biometry of the Anterior Segment of the Human Eye," *Investigative Ophthalmology & Visual Science*, vol. 38, No. 7, pp. 1304-1313 (Jun. 1997).

Huang, David, et al., "Micron-Resolution Ranging of Cornea Anterior Chamber by Optical Reflectometry," *Lasers in Surgery and Medicine*, vol. 11, pp. 419-426 (1991).

Huang, David, et al., "Optical Coherence Tomography," *Science*, vol. 254, pp. 1178-1181 (Nov. 22, 1991).

Choma, Michael A., "Sensitivity advantage of swept source and Fourier domain optical coherence tomography," *Optics Express*, vol. 11, No. 18, pp. 2183-2189 (Sep. 8, 2003).

Vergnole, Sébastien, et al., "Common Path swept-source OCT interferometer with artifact removal," *Proc. of SPIE*, vol. 6847, 8 pgs. (2008).

Hitzenberger, C.K., et al., "Measurement of Corneal Thickness by Laser Doppler Interferometry," *Investigative Ophthalmology & Visual Science*, vol. 33, No. 1, pp. 98-103 (Jan. 1992).

Omar, Basil A., et al., "Differential phase quadrature surface profiling interferometer," *Applied Optics*, vol. 29, No. 31, pp. 4715-4719 (Nov. 1, 1990).

Choma, Michael A., et al., "Instantaneous quadrature low-coherence interferometry with 3 x 3 fiber-optic couplers," *Optics Letters*, vol. 28, No. 22, pp. 2162-2164 (Nov. 15, 2003).

Rollins, Andrew M., et al., "Optimal interferometer designs for optical coherence tomography," *Optics Letters*, vol. 24, No. 21, pp. 1484-1486 (Nov. 1, 1989).

Baumgartner, Angela, et al., "Signal and Resolution Enhancements in Dual Beam Optical Coherence Tomography of the Human Eye," *Journal of Biomedical Optics*, vol. 3, No. 1, pp. 45-54 (Jan. 1998).

IPRP and Written Opinion for International Application No. PCT/EP2009/004264 dated Jan. 27, 2011.

* cited by examiner

US 9,155,462 B2

SHORT COHERENCE INTERFEROMETRY FOR MEASURING DISTANCES

PRIORITY CLAIM

The present application is a National Phase entry of PCT Application No. PCT/EP2009/004264, filed Jun. 12, 2009, which claims priority from German Application Number 102008029479.9, filed Jun. 20, 2008, the disclosures of which are hereby incorporated by reference herein in their entirety.

FIELD OF THE INVENTION

The invention relates to short-coherence interferometry methods for measuring several axially spaced regions of a sample, in particular an eye, wherein a measurement beam is directed onto the sample, beam parts are axially relatively delayed and an interference signal is generated from sample radiation formed by measurement radiation scattered or reflected back from the sample.

The invention further relates to a short-coherence interferometer apparatus for measuring two axially spaced regions of a sample, in particular an eye, which has a measurement beam path through which measurement radiation falls onto the sample, a tuning interferometer device for the axial relative delaying of beam parts and a detector device for measuring an interference signal from sample radiation formed by measurement radiation scattered or reflected back from the sample.

BACKGROUND

To measure transparent or partially transparent samples, for example of the human eye, short-coherence interferometers which operate by means of optical coherence tomography (hereinafter: OCT) are known, for example from WO 2007/065670 A1. They serve to detect the location and size of scattering centres within a sample, such as for example miniaturized optical components or biological tissue, e.g. the human eye. For an overview of the corresponding literature on OCT, reference may be made to US 2006/0109477 A1. This patent publication also describes the basic principles of OCT.

The principle of OCT comprises both embodiments in which an imaging occurs through irradiation and radiation detection by scanning at different locations across the direction of incidence of the radiation and embodiments, simplified compared with these, in which the irradiation and radiation detection is carried out only along an axis that remains unchanged and axial (i.e. 1-dimensional) scattering profiles are thus generated. The latter embodiment corresponds, as far as the image production is concerned, to a so-called A-scan of ultrasound image production; it is also called optical coherence domain reflectometry or short-coherence reflectometry (OCDR). When OCT or OCDR is mentioned here, they are to be understood to mean both scanning and OCDR systems.

To detect larger objects or to enlarge the measurement range, it is known to use an interference of several measurement beams each with a separate reference beam or to superimpose several individual measurement beams in pairs, which is also called a so-called "dual beam" interferometer. This is known from Drexler et al., "Submicrometer Precision Biometry of the Anterior Segment of the human Eye", Investigative Ophthalmology & Visual Science, June 1997, Vol. 38, No. 7.

Time-domain OCDR (TD-OCDR) with rapid-scanning reference arm and Fourier-domain OCDR (FD-OCDR) with fixed reference arm and evaluation of spectral interferences are known as variants for OCDR. The latter exists in yet another variant using broadband light sources and spectrometer-based detection (spectral domain or SD-OCDR) and in another variant using spectrally tunable light sources and broadband detectors (swept-source or SS-OCDR).

In TD-OCDR, the sample is illuminated by a short-coherent radiation and an interferometer ensures that radiation scattered back from the sample can interfere with radiation which has passed through a reference beam path. This principle, already described at a relatively early stage in Huang, et al., Micron-Resolution Ranging of Cornea Anterior Chamber by Optical Reflectometry, Lasers in Surgery and Medicine 11, 419-425 (1991), can record a depth-resolved scattering profile of the sample if the length of the reference beam path is adjusted, whereby a window corresponding to the coherence length of the radiation used is adjusted in the sample. If, as described in Huang, et al., Science 254: 1178-1181, 1991, the illuminating beam is also moved relative to the sample, a depth-resolved sectional view (tomogram) of the sample can be produced, i.e. lateral scanning optical coherence tomography (TD-OCT) is realized. The size of this window defines the maximum achievable depth resolution. For a good depth resolution, radiation sources with the shortest possible coherence, i.e. spectrally wide, are thus necessary. Because of the measurement method, only a fraction of the radiation reflected back, i.e. that scattered back from the measurement depth of the sample, which corresponds to the length of the reference beam path, is detected at any time. In known structures, therefore, over 99% of the photons scattered back from the sample are not actually detected for the measurement.

A higher yield is obtained with SD-OCDR. Here, the length of the reference beam path is no longer altered; instead, the radiation brought to interference is detected spectrally resolved. The depth information of the sample, i.e. the depth-resolved contrast signal, is calculated from the spectrally resolved signal. As a mechanism for adjusting the path length of the reference beam path is no longer necessary, the SD-OCDR technique is capable of measurement simultaneously at all depths of the sample. The thereby achieved higher yield of the radiation scattered back achieves a sensitivity up to 20 dB higher for the same measurement time. A disadvantage of SD-OCDR systems is the maximum measurement range size, which is limited by the spectrometer resolution, and the reduction in sensitivity which increases with the measurement depth. The required structure is also much more expensive.

The SS-OCDR variant, in which the spectral resolution of the interference signal with a spectrometer is dispensed with and, instead, the illumination source is spectrally tuned, requires somewhat less additional structural outlay. This method, like SD systems also, is more sensitive than TD-OCDR because of the higher photon recovery, as M. Choma et al. explain in "Sensitivity advantage of swept source and Fourier domain optical coherence tomography," Opt. Express 11, 2183-2189 (2003). In the case of SS-OCDR, the maximum resolution corresponds to the tunable wavelength range of the radiation source, and the measurement depth, i.e. the axial measurement range, is predetermined by the coherence length, i.e. the line width, of the radiation used.

A particularly compact SS-OCDR variant is to be found in S. Vergnole et al., "Common Path swept-source OCT interferometer with artifact removal", in Coherence Domain Optical Methods and Optical Coherence Tomography in Biomedicine XII, ed. J. Izatt et al., Proc. Of SPIE Vol. 6847, 68472W, 2008. Here reference radiation is produced by reflection at the end of a partly-reflective light-conducting fibre which conducts the measurement radiation onto the sample. The radiation reflected back from the sample and the reference radiation are then conducted through an interferometer the arms of which have different path lengths, and then superimposed. The path length difference defines the distance of the covered sample region from the partly-reflective end of the light-conducting fibre. To detect distances between different sample regions beyond the OCDR measurement depth, several measurements must be carried out. The use of a fibre-tip reflector as reference is also known from US 2007/0008545 A1.

In all OCDR variants, the measurement range and the measurement resolution and/or measurement accuracy are linked in a certain way. For example, in SD-OCDR the ratio between realizable spectrometer resolution and spectral width to be covered is limited. In TD-OCDR, although an adequate spectral bandwidth or sufficiently short coherence length of the radiation must also allow the resolution of sample structures of interest, the measurement range is ultimately linked via the maximum realizable scanning speed and sampling frequency to the measurement sensitivity and measurement resolution for a given measurement duration. To rectify the limitation imposed by the link, WO 2007/065670 A1 skilfully describes combining several interferometer devices which are each assembled from their own reference beam path as well as an associated sample beam path. By different matching of these several interferometer devices which, although combined in one device, are independent, measurements can be taken simultaneously at different points in the eye and thus the measurement range can be enlarged. The document further describes different approaches for differentiating the radiations in the combined interferometers, for example in respect of the polarization of the radiation or the wavelength. Such a differentiation is also described in WO 2001/038820 A1 which, however, is concerned only with TD-OCDR, thus requires moving elements for adjusting the length of the reference beam path. The principle of using several reference beam paths of different lengths can also be found in US 2005/0140981, or in U.S. Pat. No. 6,198,540, which each relate to TD-OCDR for enlarging the measurement range and use several, individually adapted reference beam paths of different lengths.

The outlay increases dramatically when a sample subjected to movements or pulsations, such as e.g. the human eye, is to be measured. Measurement must then either be carried out so rapidly that no disruptive movements or pulsations occur in the measurement duration, or such influences must be compensated.

One possibility for compensation is the already mentioned dual-beam structures/methods. Here, a measurement beam is constructed from two beam portions which would be capable of interfering with each other if they were not axially shifted towards each other. This axial shifting of the portions of the incident measurement radiation is generated by a tuning interferometer and adjusted to fit the axial distances between the sample regions to be measured. The backscatter or reflection back on the sample then removes the axial offset for the radiation portions again and the sample radiation can then interfere directly. An interference signal is thus obtained according to the known OCDR principles.

The already named US 2006/0109477 ultimately does not actually allow several regions of a sample to be covered which are axially further apart than the measurement depth, but concentrates instead on achieving the greatest possible sensitivity, for which 2×2 and 3×3 fibre couplers combined with a difference signal evaluation of quadrature components are used to realize the balanced detection.

SUMMARY OF THE INVENTION

The object of the invention is therefore to create a short-coherence interferometer arrangement or a short-coherence interferometry method which is both insensitive to axial sample movements and allows a high yield of irradiated and reflected radiation for partly-absorbing or -reflecting objects and permits effective noise suppression.

The invention achieves this object by a short-coherence interferometer apparatus for measuring several axially spaced regions of a sample, in particular an eye, which has a measurement beam path through which measurement radiation falls onto the sample, a tuning interferometer device for axially relatively delaying beam parts, wherein the axial relative delay corresponds to the axial spacing of the regions, and a detector device for generating an interference signal from sample radiation formed by measurement radiation scattered or reflected back from the sample, wherein the tuning interferometer device splits the sample radiation into two beam parts, axially relatively delays and superimposes them to obtain interference and forms during the superimposition single beams which represent the quadrature components of the sample radiation, and the detector device detects the single beams.

The invention further achieves the object by a short-coherence interferometry method for measuring several axially spaced regions of a sample, in particular an eye, wherein a measurement beam is directed onto the sample, beam parts are axially relatively delayed, the axial relative delay corresponds to the axial spacing of the regions, and an interference signal is generated from sample radiation formed by measurement radiation scattered or reflected back from the sample, the sample radiation is split into two beam parts which are axially relatively delayed and superimposed to obtain interference, single beams are formed during the superimposition which represent quadrature components of the sample radiation, and the single beams are detected. By quadrature component detection is meant, as known to a person skilled in the art, a detection of several interference signals from different superimpositions of two part-beams in which there are different phase positions between the part-beams, including the case of 180°, which is generally called "balanced detection".

The structure according to the invention thus dispenses with the pre-interferometer inherent in known dual-beam principles used to provide a radiation which consists of two portions delayed vis-à-vis each other which can interfere after passing through the sample. The structure according to the invention thus emits onto the sample not a "dual-beam" comprising two portions delayed vis-à-vis each other, but a measurement radiation which is homogeneous in its axial composition. The interference capability is created by the tuning interferometer only after the beck-reflection back or back-scattering. The problem that pre-interferometers necessarily send radiation to two outputs of the interferometer, and are thus less efficient, is thus avoided. The "post-interferometer" according to the invention with several outputs for balancing the wavelength allows additional phase information to be produced, and in addition an interferometer device as free from back reflection as possible.

The "post-interferometer", i.e. the tuning interferometer device acting on the sample radiation, which first splits the sample radiation already returning from the sample into portions delayed to different extents, is, in combination with several outputs for generating phase-shifted interference signals, a feature of the invention. The approach according to the invention manages without a fixed reference, as the reference radiation is one of the portions reflected at the sample. Independence from the movement of the sample is thereby automatic. Furthermore, the distance between the sample regions can be detected in one measurement. An additional advantage is that there is no need to match the polarization states of a reference radiation and the sample radiation.

The invention combines in the apparatus according to the invention or the method according to the invention the "dual-beam" principle with a detection of phase-shifted quadrature components of the interference signals, in particular in the form of difference signals in a "balanced detection".

This detection allows in particular in the case of TD-OCDR or SS-OCDR a suppression of disruptive constant light portions, laser radiation intensity fluctuations and a noise suppression such as is known for quadrature component detection from the publication A. Podoleanu, APPLIED OPTICS, Vol. 39, No. 1, p. 173, "Unbalanced versus balanced operation in an optical coherence tomography system".

It is possible according to the invention in particular to determine quadrature components of the interference signals with phase shifts other than 180° e.g. to suppress mirror artefacts when reconstructing FD signals, thus e.g. in the case of SS-OCDR or SD-OCDR. For this, reference is made to US 2004/0239943 which relates in general to the use of quadrature components.

The approach according to the invention realizes the "dual-beam" principle and a very high utilization of the available radiation intensity, ideally 100% in each case, i.e. all the available radiation which falls onto the eye can illuminate the sample and all the radiation scattered back from the sample is detected.

For the interferometer device, in principle any suitable structure which axially shifts a beam part of the sample radiation vis-à-vis the remaining beam part by a specific, preferably adjustable value comes into consideration. A particularly simple structure is obtained with a Mach-Zehnder interferometer which is an example of a back-reflection-free tuning interferometer. Alternatively, a Michelson interferometer can also be used.

The axial offset of the two beam parts is naturally matched to the distance between the regions to be detected. An optimum matching is achieved when the offset corresponds to exactly twice the axial distance between the regions. Here, matching relates to the optical paths, thus taking into account the refractive indices of the media in sample and tuning interferometer. As a rule, this distance is not precisely known in advance, with the result that by specifying in advance the path length by which the two beam parts are axially offset vis-à-vis each other the axial distance between the regions is selected and consequently the regions on the sample preselected. It is therefore to be preferred if the path length on the tuning interferometer device is adjustable, particularly preferably starting from a base value of +/−50% of a theoretical value of twice the axial distance between the regions, e.g. the average optical eye length.

The radiation used in the apparatus depends in respect of its spectral characteristics essentially on whether TD-, SS- or SD-OCDR is to be realized, but must in any case ensure a sufficient penetration and backscatter in the sample, such as for example through wavelengths in the range of from 700 . . . 1100 nm in the eye. It is preferred that, in addition to a radiation source providing the radiation, a coupling element is provided downstream of the radiation source, which conducts radiation coming from the radiation source as measurement radiation onto the sample and splits off measurement radiation scattered or reflected back in itself from the sample to the tuning interferometer device. The coupling element preferably comprises a circulator in order to conduct the highest possible portion of the backscattered or reflected-back measurement radiation to the tuning interferometer device. For example, a polarization-independent circulator or a combination of polarization splitter and $\lambda/4$ plate come into consideration as circulator, or Faraday rotator.

The realization of the coupling element as polarization splitter also provides a good opportunity in the case of SS-OCDR of referencing the time-dependent wavelength tuning if the coupling element splits off a part of the radiation coming from the radiation source as reference radiation which has a polarization state different from that of the measurement radiation, and conducts the reference radiation into a reference beam path at the end of which the reference object reflecting or scattering back the reference radiation is arranged, wherein the coupling element superimposes the measurement radiation reflected or scattered back in itself from the sample with the reference radiation reflected or scattered back from the reference object and conducts it to the tuning interferometer device. There can then be a superimposed measurement of the differently polarized sample and reference radiations, with the result that a simple referencing of the wavelength tuning is achieved, which increases measurement accuracy in the case of SS-OCDR. The distance between the reflectors in the reference radiation path is preferably adjusted such that the resulting wavelength reference signal cannot superimpose the sample signal to be measured in a disruptive manner, e.g. by having the wavelength reference signal generate peaks only at measurement depths where sample signals are not to be expected.

It is known that a particularly compact structure is achieved with fibre-optic elements.

It is therefore to be preferred that the coupling element is based on fibre optics. In the interests of a high yield, optionally the fibre end emitting the measurement radiation, or very generally the coupling element, can reduce reflection and/or be antireflective—in the case of a fibre e.g. through a angled polish.

It is further preferred in the case of fibre-optic construction that the tuning interferometer device splits the measurement radiation scattered or reflected back from the sample into the two beam parts by means of a 2×2 fibre splitter, sends the beam parts through light-conducting fibres of different lengths and conducts them into a 2×2 fibre splitter, a 2×3 fibre splitter or a unit of two 2×2 fibre splitters at the outputs of which the single beams emerge.

In the case of a 2×3 fibre splitter, there are three outputs, each with 120° phase-shifted interference signals, which are suitable for carrying out a complex SS-OCDR reconstruction. This configuration is suitable in particular for eliminating artefacts (mirror artefacts) which would otherwise result from indeterminable phase signs. This procedure is known from US 20040239943. The quadrature component detection, like the balanced detection with 180° phase shift, further suppresses specific noise portions caused by the source, which is advantageous in particular in the case of low-intensity arrangements, when therefore only a small portion of the measurement radiation is scattered or reflected back from the sample.

If the tuning interferometer device is purely fibre-optic, using only a single type of fibre, the path length difference of the fibres also causes a dispersion difference. Although this is disruptive for TD-OCDR methods, as the interference signals would thereby be reduced, it is favourable for the realization of FD-OCDR methods, as the dispersion difference is suitable for marking and suppressing mirror artefacts during reconstruction, as already described in US 2006/0171503. If, however, the dispersion difference is to be minimized, for example to maximize TD-OCDR signals, fibres or fibre parts of differing dispersions can also be used and the fibre lengths set to compensate while preserving the path length difference. The shorter fibre is the one that has the higher dispersion.

It is understood that the features named above and still to be explained below can be used not only in the given combinations, but also in other combinations or on their own, without going beyond the framework of the present invention.

BRIEF DESCRIPTION OF THE DRAWINGS

The invention is explained in further detail below by way of example using the attached drawings which also disclose features essential to the invention. There are shown in.

DETAILED DESCRIPTION

Figure 1:
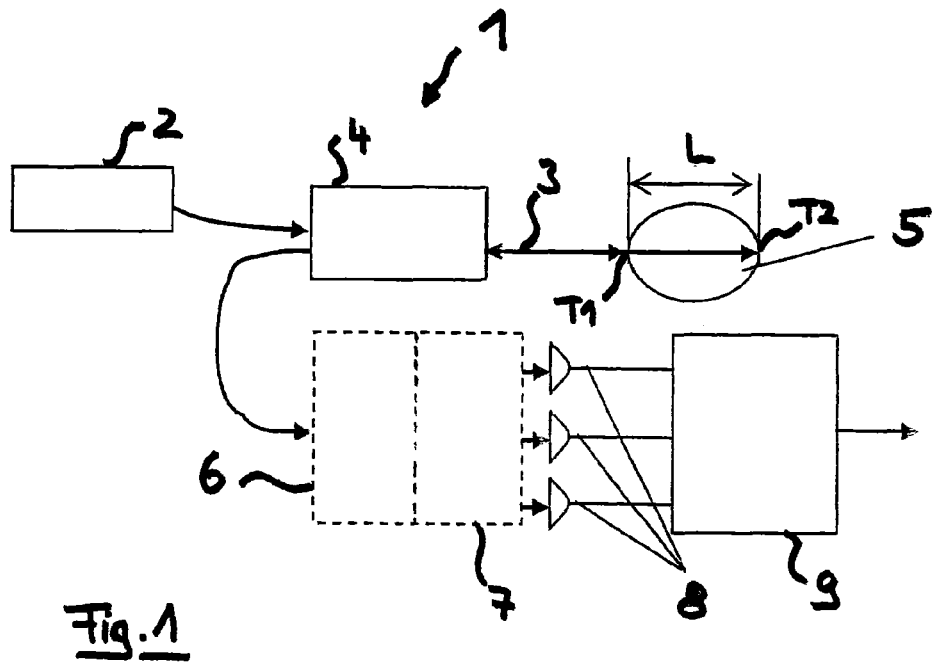
FIG. 1 is a schematic representation of a short-coherence interferometer device.

FIG. 1 shows schematically an interferometer apparatus 1 in the form of an eye-length measuring device, wherein this realization relates merely to an exemplary field of application of the interferometer apparatus 1, to which extent it is not be understood as limitative.

In apparatus 1, radiation of a radiation source 2 is conducted as measurement radiation 3 into a measurement beam path where it is directed onto the measurement object, here formed by an eye 5, i.e. the sample. The sample has axially spaced regions, here represented schematically as regions T1 and T2 of the eye 5, for example the front surface of the cornea, the rear surface of the cornea, the front surface of the lens, the rear surface of the lens or the fundus. Starting from the vertex of the front surface of the cornea as region T1 and the fundus as region T2, the axial distance between these regions gives the optical eye length L. The illumination of the areas T1 and T2 can also be influenced with single- or multiple-focussing elements to optimize the backscatter, wherein the multiple-focussing elements can also comprise segmented lenses or diffractive optical elements, as described for example in DE 446183 B4.

Both regions T1 and T2 scatter back measurement radiation in the form of sample radiation which back-scattering is indicated by the double arrow in the measurement beam path. The measurement beam generated from the radiation of the laser source 2 falls onto the eye 5 through a coupling device 4 the function of which is to separate the sample radiation from the measurement radiation as efficiently as possible. The coupling device 4 thus, without unnecessary attenuation, i.e. (if an attenuation is not deliberately to take place) with the highest possible degree of transmission, conducts measurement radiation from the laser source 2 to the eye 5 onto the at least two spaced regions T1 and T2. The sample radiation scattered back from these regions is then in turn conducted as efficiently as possible from the coupling device 4 to a tuning interferometer device 6 arranged downstream which operates as free from back reflection as possible, i.e. returns no radiation to the coupling device 4. The tuning interferometer device consists of two function sections, namely a section 6 splitting the sample radiation into two beam parts as well as a section 7 superimposing the separated beam parts again, wherein the two beam parts travel over different path lengths between separation and superimposition. The tuning interferometer device thus effects a fixed or variable path length difference between the two beam parts of the sample radiation, wherein the path length difference is matched such that light portions scattered back between the regions T1 and T2 can interfere. An additional effect of the second section 7 of the tuning interferometer device is that during the superimposition there are at least two phase-shifted single beams, which correspond to quadrature components of the interfering radiation at the outputs of the second section 7 of the tuning interferometer device. With the help of these quadrature components, which are present as electric signals in quadrature signal lines 8 following the electrical detection of the single beams, an evaluation device 9 effects an OCDR reconstruction which realizes TD-, SS- or SD-OCDR depending on the principle applied. Naturally, the detectors not described in more detail are formed to match, i.e. in the case of SD-OCDR there is a spectral analysis of the single beams. This is known to a person skilled in the art, however, and need not be explained here in more detail.

Figure 2:
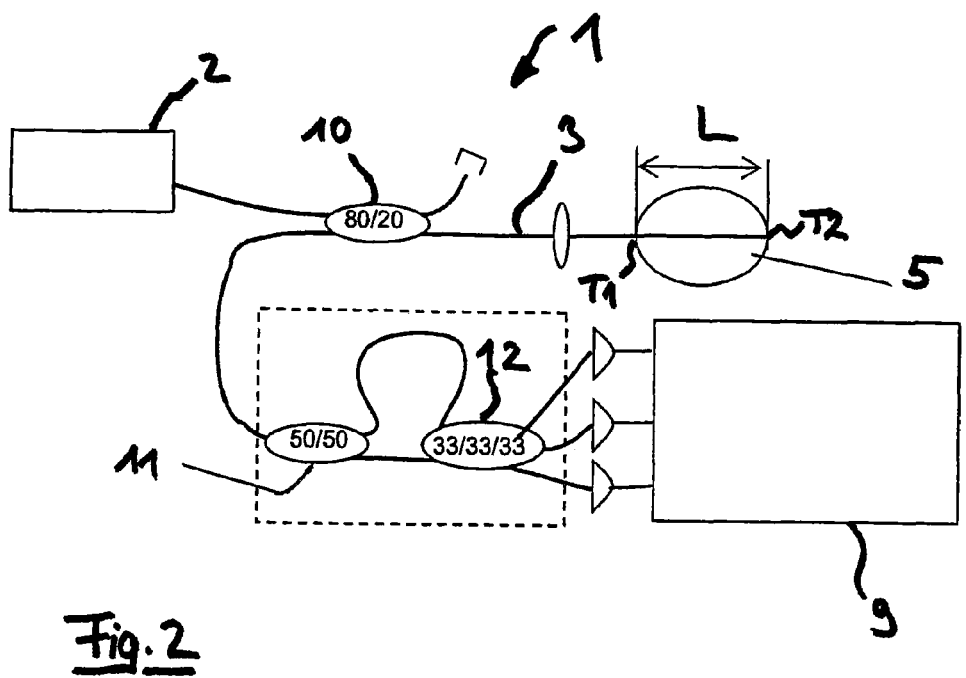
FIG. 2 is a representation of a fibre-optic realization of the apparatus of FIG. 1.

FIG. 2 shows a fibre-optic embodiment example of apparatus 1 of FIG. 1. In FIG. 2, as in the subsequent figures, elements which have the same function or the same construction as elements from other embodiment examples are given the same reference numbers and will therefore not be described yet again.

FIG. 2 is, as already mentioned, based on fibre optics and provided purely by way of example for SS-OCDR. The laser source 2 is therefore tunable. The coupling device is realized here as a polarization-independent circulator or as a fibre coupler 10, e.g. with an 80/20 split. However, other splits are also possible, for example 70/30 to 95/5. The latter configuration is particularly suitable when the radiation of the laser source 2 must be attenuated to 5% to 30% before striking the sample. The tuning interferometer device is formed as a fibre-optic Mach-Zehnder interferometer with a 50/50 fibre splitter 11 as well as a 2×3 fibre coupler 12 which delivers at its three outputs single beams each phase-shifted by 120°, which stem from an interference. This interference therefore stems from the fact that the path length difference of the Mach-Zehnder interferometer corresponds to approximately twice the average optic axis length L and the OCDR measurement depth is sufficient to cover the variation in eye lengths (approx. ±13 mm).

Using the 120° phase-shifted single beams that are recorded on detectors, the evaluation device 9 carries out a complex SS-OCDR reconstruction, e.g. according to US 2004/0239943.

Figure 3:
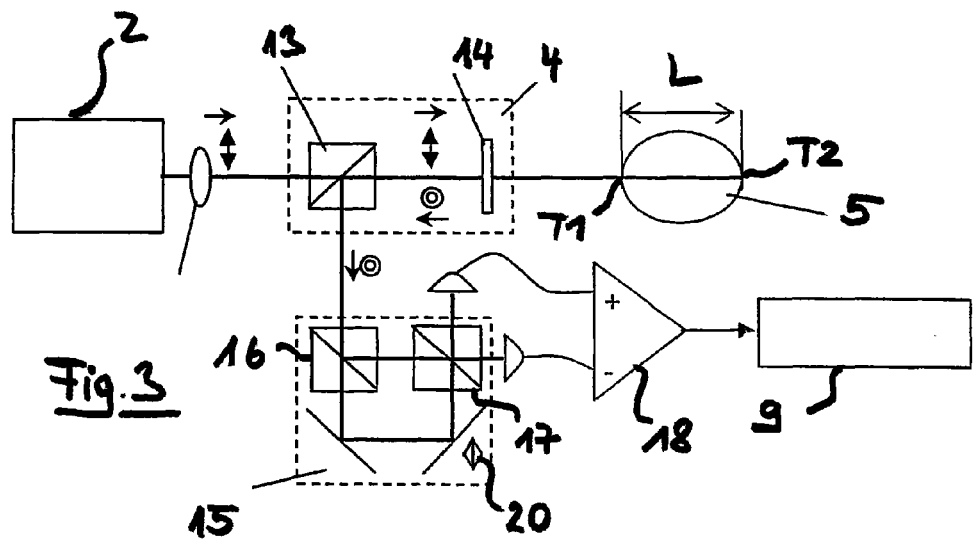
FIG. 3 is an apparatus similar to that in FIG. 1, but with circulator or rotator add-ons for particularly high measurement radiation utilization.

FIG. 3 shows a second variant, here as a free-beam structure. This structure provides two interference signals phase-shifted by 180° and achieves a particularly high yield because the coupler 4 is now formed from a polarization splitter 13 and a λ/4 plate 14 in the style of a circulator or Faraday rotator. Linear-polarized measurement radiation coming from the laser source 2 passes through the polarization splitter 13 in full due to this polarization state. After passing through the λ/4 plate the radiation is first polarized in circular manner and, after back reflection at the eye and a further passage through the λ/4 plate, transformed into a state which is polarized orthogonally linear to the initial state, which is illustrated by a circular symbol in FIG. 3. The polarization splitter reflects this radiation, which is polarized orthogonal to the initial state, fully out of the beam path with the result that 100% of the measurement radiation provided by the laser source 2 falls onto the eye, and also all the sample radiation reflected and scattered back at the eye is conducted to the tuning interferometer device which is formed here as a tuning interferometer device 15 free from back reflection and comprises beam splitters 16 and 17. The path length difference can be adjusted, as indicated by the double arrow 20.

The variable path length difference allows the TD-OCDR principle to be used for example, in particular also applying the double filtering principle described for example in Hitzenberger et al. *Investigative Ophthalmology & Visual Science*, Vol. 33, No. 1, January 1992. When the structure is designed for SS-OCDR or SD-OCDR, the path length adjustment can also make possible a selection from the regions T1 and T2 to be covered.

The interference signals phase-shifted by 180° are amplified in a differential amplifier 18 within the meaning of a balanced detection and delivered to the evaluation device 9.

The mentioned high radiation yield of the structure of FIG. 3 obtains above all when the sample changes the polarization of the radiation by only a little. Otherwise, a polarization compensator is optionally to be arranged in front of the eye. Polarization compensation can also be applied between the arms of the tuning interferometer when for example changes in the polarization state due to stress-induced birefringence in bent fibres must be compensated or the light portions that are to be brought to interference from the sample regions T1 and T2 have experienced different polarization state changes there.

Figure 4:
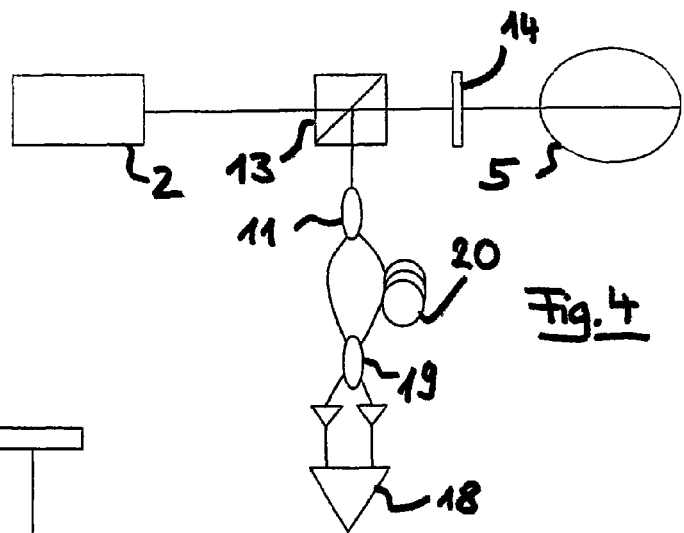
FIG. 4 depicts a construction similar to FIG. 2, but with only two quadrature components.

In a development it is possible to have a purely fibre-optics-based tuning interferometer device using a single type of fibre. This structure is shown in FIG. 4. It is possible (unlike that shown in FIG. 4) to also have a fibre-optics-based beam splitter 3, as in principle in the structures and methods described here fibre-optic components can be replaced by free-beam optic components as required, or any mixed forms of free-beam and fibre optics are possible.

The path length difference, which, here also, can be designed adjustable by e.g. a fibre-stretching path length adjuster 20, also results in a dispersion difference. However, for the FD-OCDR variants, i.e. SS-OCDR and SD-OCDR, such a dispersion difference is advantageous, as they are suitable for marking and suppressing mirror artefacts during reconstruction.

Figure 5:
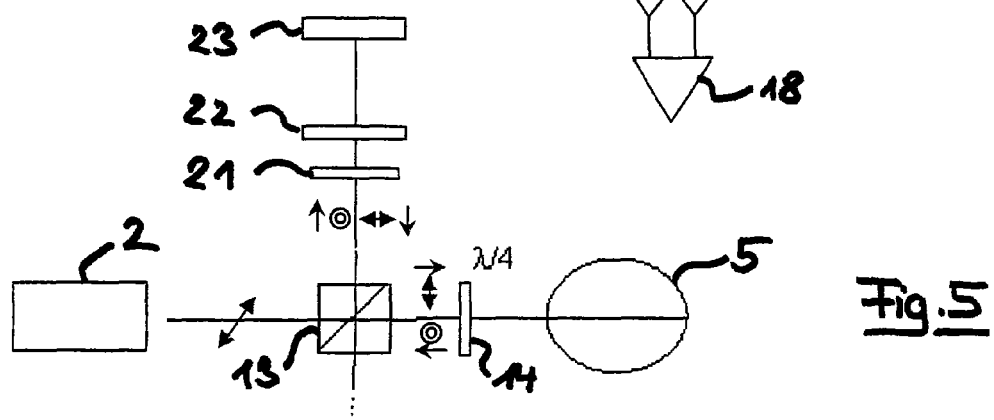
FIG. 5 depicts a possible variation of one of interferometers of FIGS. 1 to 4 for referencing a wavelength tuning and FIG. 6 depicts a further construction of the apparatus of FIG. 1.

If a polarization splitter is used as coupling device 4, a reference structure can also be measured parallel to the sample and the corresponding sample radiations or reference radiations returning from the reference structure or the sample can be detected not interfering with each other in the same tuning interferometer as well as the same detector device. This variation, which is possible in principle for all structures, is shown in FIG. 5. The coupling apparatus 4, here again designed as pole splitter 13, also splits a part of the measurement radiation emitted from the laser source 2 as reference radiation into a reference arm which, like the sample arm also, has a λ/4 plate 21. Reference reflectors 22 and 23 a defined distance apart represent an example of a reference object the independent detection of which, as already described, takes place in a tuning interferometer, but with suitable polarization difference in the detection. In particular with SS-OCDR variants, this approach allows a referencing of the time-dependent wavelength tuning.

If the contrast of the polarization splitter 13 (typically 20 . . . 30 dB) compared with the desired signal dynamic is insufficient, in addition to the suppression, according to the polarization, of the interfering interaction between sample radiation and radiation from the reference object, the position of the reference reflectors can also be altered jointly vis-à-vis the sample position such that the radiation from sample and reference arm can no longer interfere, as the path difference is too great. The wavelength reference signal is not altered by the preservation of the distance between the reflectors 22 and 23.

Figure 6:
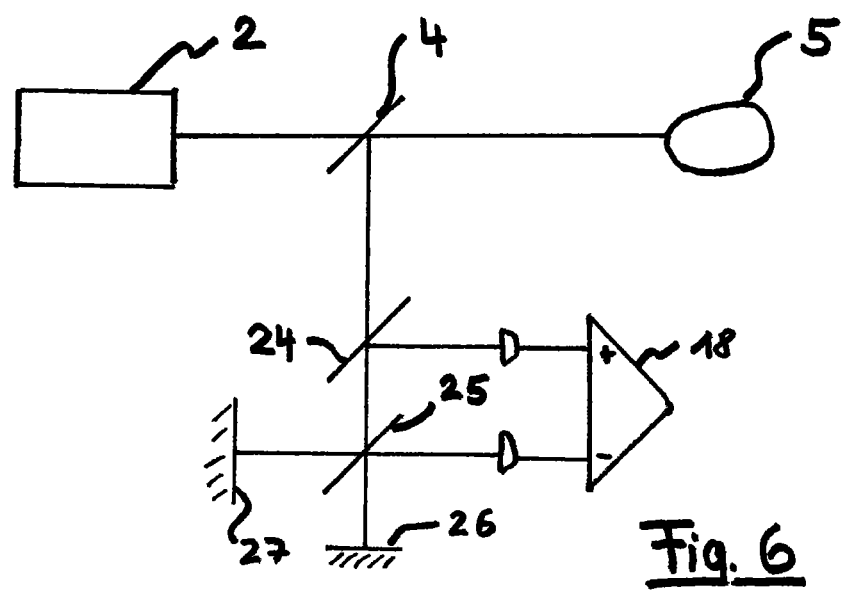

FIG. 6 shows a further variant in which the tuning interferometer device 6 is formed as a Michelson interferometer. The radiation from the coupling device formed as (optionally not polarization-separating) splitter 13 is split in a beam splitter 24 into a part which passes through a Michelson structure having a beam splitter 25 and mirrors 26, 27. The interfering radiation portions of the sample radiation then lie at the detectors.

In principle, it is true of all embodiments with polarization optics that, when there is a depolarizing or polarization-altering action of the sample (it is approximately 10% in the eye), a sample-specific polarization matching of polarization-optical elements in embodiments of the described apparatusses should be carried out in order to ensure a sufficiently high transmission through the mentioned polarization-optical elements. In addition, a fixed-set state can also be used, e.g. with regard to the orientation of polarization splitters, waveplates etc.

The invention claimed is:

1. A Short-coherence interferometry method for measuring two axially spaced regions of a sample or an eye, comprising
using a radiation source providing measurement radiation and using a coupling element;
performing polarization splitting of the measurement radiation coming from the radiation source by the coupling element into a measurement beam and a reference radiation which has a polarization state different from the measurement beam;
directing the measurement beam onto the sample or the eye;
collecting sample radiation formed by measurement radiation scattered or reflected back from the sample or the eye;
providing a reference beam path at the end of which is arranged a reference object that reflects or scatters back radiation conducted into reference beam path;
arranging the coupling element between the radiation source and the sample such that the coupling element conducts the measurement beam to the sample and receives the collected sample radiation, and conducts the reference radiation into the reference beam path and receives the reference radiation returning from the reference radiation beam path, and superimposes the sample radiation with the received reference radiation;
splitting the superimposed sample and reference radiation into two beam parts;
axially relatively delaying the two beam parts with a delay predefining a range of distance between the spaced regions;
superimposing the two beam parts to generate an interference signal;
setting a path length of the axial relative delay such that the two superimposed beam parts of the sample radiation interfere;

forming single beams which represent quadrature components of the interfering beam parts during the superimposition;

detecting the single beams with the sample radiation and the reference radiation not interfering with each other and determining the quadrature components therefrom;

deducing the axial distance between the regions from the path length of the axial delay and the determined quadrature components.

2. The method according to claim 1, wherein the two beam parts are axially offset by using a Mach-Zehnder interferometer or a Michelson interferometer.

3. The method according to claim 1, wherein the path length is chosen or adjusted to be equal to twice an average eye optical length.

4. The method according to claim 1, further comprising including a circulator in the coupling element.

5. The method according to claim 1, further comprising carrying out a TD-OCDR, SS-OCDR or FD-OCDR reconstruction of the quadrature components and generating a signal which reproduces the axial distance between the axially spaced regions.

6. The method according to claim 1, further comprising detecting the single beams from the sample radiation and the reference radiation not interfering with each other on a single detector.

7. The method according to claim 1, further comprising using a swept source as the radiation source and sweeping a wavelength of the radiation.

8. A Short-coherence interferometer apparatus for measuring two axially spaced regions of a sample or an eye, comprising:

a radiation source providing measurement radiation;

a measurement beam path through which the measurement radiation falls onto the sample or the eye and which collects sample radiation formed by measurement radiation scattered or reflected back from the sample or the eye;

a reference beam path at the end of which is arranged a reference object that reflects or scatters back radiation conducted into reference beam path;

a coupling element, wherein the coupling element is arranged downstream of the radiation source, conducts the measurement radiation into the measurement beam path and receives the collected sample radiation, wherein the coupling element is formed by a polarization splitter and splits off a part of the measurement radiation coming from the radiation source as reference radiation to provide for a time-resolved wavelength referencing, the reference radiation having a polarization state different from the measurement radiation, and conducts the reference radiation into the reference beam path and receives the reference radiation returning from the reference radiation beam path, wherein the coupling element further superimposes the received sample radiation with the received reference radiation;

a tuning interferometer that receives the sample radiation and reference radiation and splits the superimposed sample radiation and reference radiation into two beam parts, delays the two beam parts axially relatively by a path length and superimposes the delayed two beam parts;

wherein the tuning interferometer provides for the path length of the axial relative delay to be such that the two superimposed beam parts interfere for the axially spaced regions of the sample or the eye, and wherein, the tuning interferometer forms single beams during the superimposition which represent quadrature components of the interfering beam parts, a detector device that detects the single beams and measures an interference signal with the sample radiation and the reference radiation not interfering with each other; and a control device for the interferometer apparatus, wherein the control device determines the quadrature components from the single beams and deduces axial spacing between the regions from the path length and the determined quadrature components.

9. The apparatus according to claim 8, wherein the tuning interferometer comprises a Mach-Zehnder interferometer or a Michelson interferometer which axially offsets the two beam parts by the path length.

10. The apparatus according to claim 9, wherein the tuning interferometer provides for a path length corresponding to about twice an average eye optical length or wherein the path length is adjustable.

11. The apparatus according to claim 9, wherein the tuning interferometer is adjustable in respect of the path length and the control device controls the tuning interferometer for setting the path length.

12. The apparatus according to claim 8, wherein the coupling element comprises a circulator.

13. The apparatus according to claim 8, wherein the coupling element comprises fibre optics including a fibre end emitting the measurement radiation between the coupling element and the sample or eye, the fiber end being designed to minimize reflection.

14. The apparatus according to claim 13, wherein the fiber end is at least one of angle polished and coated.

15. The apparatus according to claim 8, wherein the tuning interferometer comprises:

a first fibre splitter that is a 2×2 fibre splitter that splits the sample radiation into the two beam parts, two light-conducting fibres of different lengths connected with the first splitter that conduct the two beam parts, and a second fibre splitter that is a 2×2 fibre splitter, a 2×3 fibre splitter or a unit of two 2×2 fibre splitters, wherein the second fibre splitter is connected to the two light-conducting fibres and outputs the single beams.

16. The apparatus according to claim 8, wherein the apparatus is formed for FD-OCDR and the tuning interferometer comprises fibre optics of only one type of fibre thus generating a dispersion difference of the two beam parts to suppress resultant mirror artefacts.

17. The apparatus according to claim 8, wherein the single beams from the sample radiation and the reference radiation not interfering with each other are detected on a single detector.

18. The apparatus according to claim 8, wherein the radiation source comprises a swept source emitting radiation swept in wavelength.

19. The method according to claim 7, further comprising measuring a wavelength of the swept source by application of the tuning interferometer.

20. The apparatus according to claim 18, wherein the tuning interferometer measures the wavelength of the swept source.

\* \* \* \* \*